United States Patent [19]

Nelson et al.

[11] Patent Number: 4,792,570
[45] Date of Patent: Dec. 20, 1988

[54] 3- AND 4-BIPHENYLOXYAMINOALKANES AND RELATED COMPOUNDS AS ANTI-INFLAMMATORY AND ANALGETIC AGENTS

[75] Inventors: Peter H. Nelson; James P. Dunn, both of Los Altos; Stefan H. Unger, Palo Alto, all of Calif.; Thomas R. Thieme, Independence, Oreg.

[73] Assignee: Syntex (U.S.A.) Inc., Palo Alto, Calif.

[21] Appl. No.: 597,790

[22] Filed: Apr. 6, 1984

[51] Int. Cl.$^4$ ............... A61K 31/205; A61K 31/135
[52] U.S. Cl. ..................... 514/651; 514/210; 514/212; 514/239.2; 514/255; 564/337; 564/347; 564/352; 564/353
[58] Field of Search ............ 564/337, 347, 352, 353; 424/330, 316; 260/501.8; 514/216; 512/212, 227, 255, 651

[56] References Cited

U.S. PATENT DOCUMENTS

| | | | |
|---|---|---|---|
| 2,187,723 | 1/1940 | Alquist et al. | 564/337 |
| 2,217,660 | 10/1940 | Alquist et al. | 564/337 |
| 2,252,828 | 8/1941 | Alquist et al. | 564/337 |
| 2,683,719 | 7/1954 | Kerwin et al. | 564/347 X |
| 3,139,456 | 6/1964 | Tweit et al. | 564/353 |
| 3,816,430 | 6/1974 | Santilli et al. | 564/352 |
| 4,064,125 | 12/1977 | Krapcho | 564/353 X |
| 4,071,559 | 1/1978 | Kikumoto et al. | 564/337 |

Primary Examiner—Robert V. Hines
Attorney, Agent, or Firm—Tom M. Moran; Ellen J. Wise; Alan M. Krubiner

[57] ABSTRACT

Compounds useful for treating inflammation, swelling and associated pain, represented by the formula:

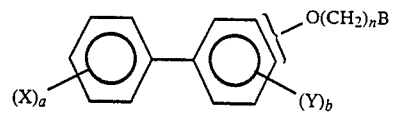

and the pharmaceutically acceptable acid addition salts thereof, wherein:
a is an integer of 0-3;
b is an integer of 0-2;
n is an integer of 3-12;
each X and each Y are independently -halo, $-R^1$, -alkoxy, or -phenyl; and
B is selected from the group consisting of:
$-NR^1R^2$, $-NR^1(CH_2CH_2OH)$,

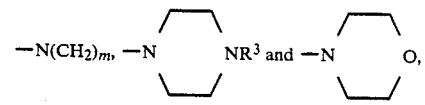

in which
$R^1$ and $R^2$ are independently H, alkyl or cycloalkyl;
$R^3$ is H, alkyl or $-CH_2CH_2OH$; and
m is an integer of 3-8.

Novel compounds are those wherein n is at least 6 if both a and b are 0.

34 Claims, No Drawings

3- AND 4-BIPHENYLOXYAMINOALKANES AND RELATED COMPOUNDS AS ANTI-INFLAMMATORY AND ANALGETIC AGENTS

BACKGROUND OF THE INVENTION

This invention concerns anti-inflammatory and analgetic agents which are 3- and 4-biphenyloxyaminoalkanes.

Anti-inflammatory and analgetic activity has teen demonstrated by compounds representing a variety of structural classes, including, for example, the corticosteroids, aspirin and related compounds, derivatives of arylacetic and arylpropionic acids, and relatives of phenylbutazone. However, no representative of any of these classes of compounds is regarded as ideal.

It has now been discovered that certain biphenyloxyaminoalkanes and related compounds exhibit useful anti-inflammatory and associated analgetic activity.

SUMMARY OF THE INVENTION

One aspect of the invention concerns novel compounds of the formula

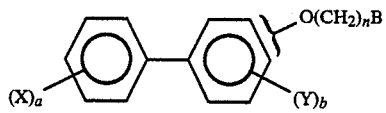

and the pharmaceutically acceptable acid addition salts thereof, wherein:

a is an integer of 0-3;
b is an integer of 0-2;
n is an integer of 3-12;
each X and each Y are independently -halo, $-R^1$, -alkoxy, or -phenyl; and
B is selected from the group consisting of:
$-NR^1R^2$, $-NR^1(CH_2CH_2OH)$,

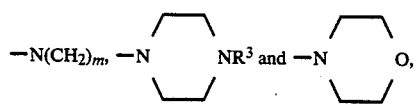

in which $R^1$ and $R^2$ are independently H, alkyl or cycloalkyl;
$R^3$ is H, alkyl or $-CH_2CH_2OH$; and
m is an integer of 3-8, with the proviso that n is at least 6 if both a and b are zero.

In two other aspects, the invention relates to pharmaceutical compositions containing a compound of Formula I or a pharmaceutically acceptable salt therof in admixture with one or more pharmaceutically acceptable excipients, and to methods of preventing, reducing or inhibiting inflammation and associated pain with compounds of Formula I, wherein a, b, X, Y, B, $R^1$, $R^2$, $R^3$ and m are as defined above, and n is independently an integer of 3-12.

Yet another aspect of the invention relates to methods of treating localized inflammation and associated pain through topical administration of compounds of Formula I, or pharmaceutically acceptable salts thereof, wherein a, b, X, Y, B, $R^1$, $R^2$, $R^3$ and m are as defined above, and n is independently an integer of 3-12.

Finally, the invention relates to a process for the preparation of compounds of Formula I and their salts.

DETAILED DESCRIPTION OF THE INVENTION

Definitions

As used herein:

"Alkyl" means a branched or unbranched saturated hydrocarbon chain containing 1-8 carbon atoms, such as methyl, ethyl, propyl, isopropyl, tert-butyl, butyl, n-hexyl, n-heptyl, iso-octyl and the like.

"Alkoxy" means the group -OR wherein R is alkyl as herein defined.

"Cycloalkyl" means a saturated carbocyclic ring containing 5-7 carbon atoms, such as cyclopentyl, cyclohexyl, and cycloheptyl.

"Optional" or "optionally" means that the subsequently described event or circumstance may or may not occur, and that the description includes instances where said event or circumstance occurs and instances in which it does not. For example, "optionally substituted hydroxybiphenyl" means that the hydroxybiphenyl may or may not be substituted and that the description includes both unsubstituted hydroxybiphenyl and substituted hydroxybiphenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

"$-N(CH_2)m$" means a radical, heterocyclic in structure, having one nitrogen and 3-8 carbons in the heterocyclic ring, such as azetidine, pyrrolidine, piperidine, etc.

"Halo" refers to bromo-, chloro-, fluoro- and iodo-.

The compounds of the invention herein contain an amino nitrogen on the alkyl side chain at which acid addition salts can be formed. "Pharmaceutically acceptable acid addition salts" refers to those salts which retain the biological effectiveness and properties of the corresponding free bases and which are not biologically or otherwise undesirable. They are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

"Biphenyl nucleus" means the aromatic phenyl-phenyl ring portion of the compounds of the invention.

The numbering system for the biphenyl nucleus is shown below:

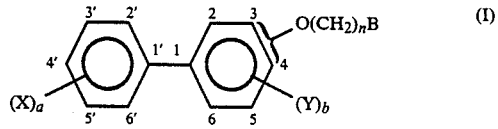

The alkoxyamino side chain, $-O(CH_2)_nB$, is attached at either of positions 3—or 4—of the biphenyl nucleus.

The "X" and "Y" substituent(s) may be positioned at any of positions 2- to 6- and 2'-to 6'- of the biphenyl nucleus, with the exception of the carbon atom at which the alkoxyamino side chain is attached.

The compounds of the invention will be named as biphenyloxyaminoalkanes. Following are examples of how representative compounds are named:

A compound of Formula I wherein n is 6, B is -N,N-dimethylamino-, a and b are 0, and the alkoxyamino side chain is in the 3- position is named "6-(3-biphenyloxy)-1-dimethylaminohexane."

A compound of Formula I wherein n is 5, B is amino-, a and b are 0, and the alkoxyamino side chain is in the 4- position is named "5-(4-biphenyloxy)-1-aminopentane."

A compound of Formula I wherein b is 2, Y is fluoro in the 2- and 6- positions, a is 0, n is 8, B is pyrrolidino-, and the alkoxyamino side chain is in the 4- position is named "8-(2, 6- difluoro-4-biphenyloxy)-1-pyrrolidinooctane".

A compound of Formula I wherein a is 1, b is 1, X and Y are each methoxy in the 2- and 2'- positions, n is 6, B is hydroxyethylamino- and the alkoxyamino side chain is in the 3- position is named "6-(2-, 2'-dimethoxy-3-biphenyloxy)-1-(2-hydroxyethylamino) hexane."

Method of Preparation

The compounds of the invention (compounds of Formula I) can be prepared by the procedures described hereinbelow and illustrated by the following reaction scheme:

of these and other syntheses of hydroxybiphenyls are well described in the chemical literature. One method for the synthesis of substituted biphenyl compounds is the coupling together of two suitably substituted benzenoid compounds, as described in *The Chemistry of Carbon Compounds* by E. H. Rodd, 1st Edition, Vol. IIIB, p 1029, 2nd Edition, Vol. III F, p 1, and in *Chemical Reviews*, 1964, p 613. These references describe the syntheses of a number of substituted hydroxybiphenyls and, in addition, the syntheses of a large number of diversely substituted biphenyl compounds which can, by methods well known to those skilled in the art, be converted into substituted hydroxybiphenyls. For example, the above references describe the preparation of many alkoxy-substituted biphenyls which can, by means of well known dealkylation reactions, as described in *Synthetic Organic Chemistry*, by R. B. Wagner and H. D. Zook, p 171, be converted into substituted hydroxybiphenyls. Similarly, amino-substituted biphenyls can be converted into the corresponding substituted hydroxybiphenyls by means of well-known diazotization reactions which are described in *Synthetic Organic Chemistry, ibid.*, p 168. The substituted amino biphenyls used for the above diazotization reactions can be obtained by reduction of the corresponding substituted nitrobiphenyls, preparations of which are described in *The Chemistry of Carbon Compounds* and in *Chemical Reviews*, referenced above. Using the above-described

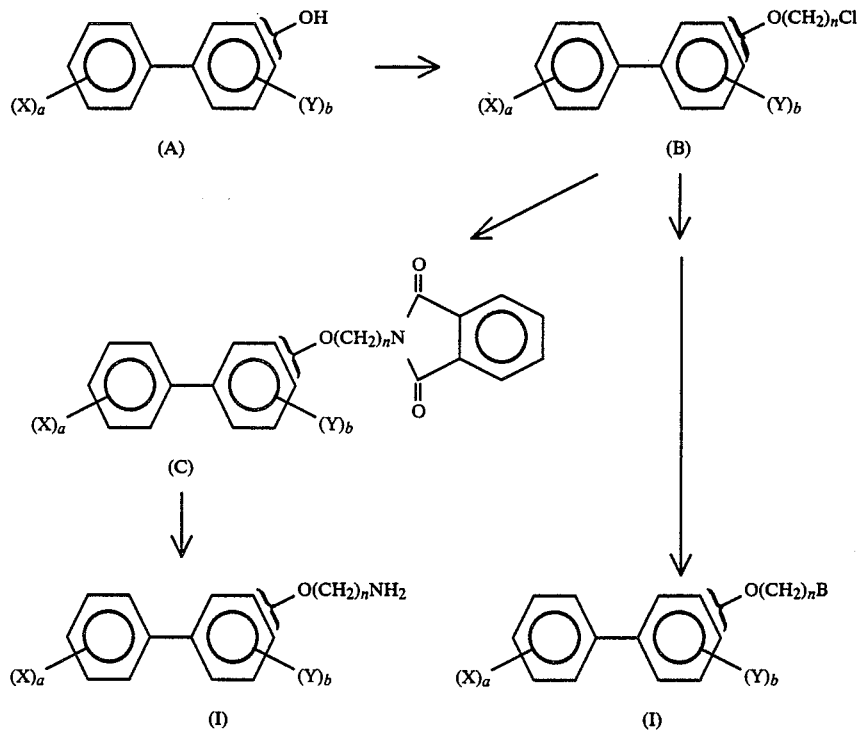

The compounds of Formula I are prepared from the corresponding optionally substituted hydroxybiphenyls of Formula A. Unsubstituted hydroxybiphenyl as well as many of the substituted hydroxybiphenyl starting materials, are commercially available. Alternatively, appropriately substituted hydroxybiphenyls can be obtained by well known synthetic procedures described in the chemical literature. In general, synthesis of hydroxybiphenyls can be accomplished by the same types of reactions by which phenols can be obtained from benzenoid starting materials. In addition, specific descriptions procedures, and others well known to those skilled in the art, hydroxybiphenyls bearing alkyl, halo and alkoxy substituents, and combinations of these substituents, can be made. In addition, hydroxybiphenyls bearing halogen substituents can be made by direct halogenation of hydroxybiphenyls, as described in the Journal of the American Chemical Society, 1934, Vol. 56, p. 202. Many hydroxybiphenyls, especially those bearing alkyl substituents, can also be made by palladium-catalysed coupling reactions between an appropriately substituted bromobenzene and an appropriately substituted phenylboronic acid, as described in Synthetic Communications, 1981, Vol. 11, p. 513, followed by a dealkylation reaction, as described above, to liberate the substituted hydroxybiphenyl. Reactions of this type are described in Preparations 1 and 2, below.

To prepare the compounds of the invention, the optionally substituted hydroxybiphenyl of Formula A is first converted to the corresponding 3- or 4- biphenyloxy alkyl chloride compound of Formula B by reaction with an ω-chloroalkylsulphonate, as shown in Reaction Scheme II:

Reaction Scheme II

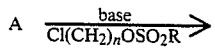

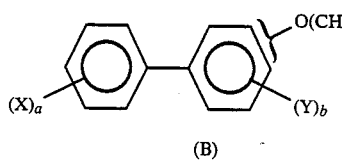

(B)

The ω-chloroalkyl sulphonate used as a reagent in the above reaction is obtained from the corresponding ω-chloroalkanol, by reaction of the alkanol with one molar equivalent of an alkyl or arylsulphonyl chloride in a basic organic solvent. The length of the alkyl chain of the ω-chloroalkanol compound determines the number (n) of carbon atoms in the alkoxyamino side chain of the final compound of Formula I. Chain lengths of 6–10 carbon units are preferred, with 6–8 being especially preferred. The ω-chloroalkanol compounds are commercially available, or can be readily prepared by reaction between an appropriate α,ω-diol, such as decane-1,10-diol, and hydrochloric acid, as described in the Journal of the American Chemical Society, Vol. 66, p. 1821, (1944) and the Journal of Organic Chemistry, Vol. 18, p. 1356, (1953). Any suitable alkyl or arylsulphonyl chloride, such as paratoluenesulphonyl chloride, benzenesulphonyl chloride, or methanesulphonyl chloride, can be reacted with the ω-chloroalkanol to form the ω-chloralkylsulphonate. A preferred reagent is paratoluenesulphonyl chloride. The reaction takes place in a basic organic solvent such as triethylamine or, preferably, pyridine, at 0°–25° C., preferably 5° C., for about 1–12, preferably about 2, hours.

The compound of Formula A is then reacted with about 1.0–1.3, preferably about 1.05, molar equivalents of the chosen ω-chloroalkylsulphonate, preferably p-toluenesulphonate, in a polar aprotic organic solvent such as tetrahydrofuran, formamide, or, preferably, N,N-dimethylformamide. The reaction takes place in the presence of from about one to about five molar equivalents of an inorganic base such as sodium hydroxide, or, preferably, about 5 molar equivalents of potassium carbonate. The reaction is conducted at a temperature of about 25°–125° C., preferably about 70° C., over a period of about 2–48 hours, preferably about 22–26 hours. The resulting product of Formula B, a 3- or 4-biphenyloxyalkyl chloride, is isolated by conventional means.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, or a combination of these proecdures. Specific illustrations are described in the Exaples. However, other equivalent separation or purification procedures can be used.

The salt products are also isolated by conventional means. For example, the reaction mixtures can be evaporated to dryness and the salts then further purified by standard methods such as those listed above.

The compounds of Formula B are then converted to the desired compounds of Formula I by treating with the appropriate reagent, as described in Sections A and B, below.

A. Compounds of Formula I

Compounds of Formula I are prepared by treating the optionally substituted compound of Formula B with ammonia or another appropriate amine, thereby converting the halo- group to the corresponding nitrogen containing substituent. This reaction is shown below:

Reaction Scheme III

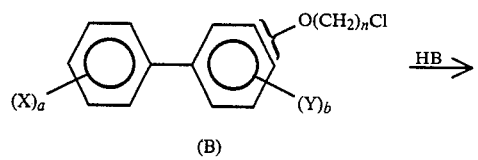

(B)

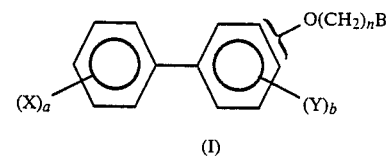

(I)

To carry out this conversion, the compound of Formula B is dissolved in, and reacted with, a solution of about 5–25 molar equivalents of the appropriate cyclic or acyclic amine, preferably acyclic, and most preferably dimethylamine. This reaction may be performed with or without the presence of a polar organic solvent, water, or mixtures thereof, such as methanol, aqueous ethanol, or preferably, ethylene glycol. The reaction takes place at a temperature of about 60°–180° C., preferably about 100° C., for about 1–8 hours, preferably about 3 hours, at a pressure of about 1–5 atomspheres, preferably at atmospheric pressure. When the reaction is substantially complete, the product compound of Formula I is isolated by conventional means, and if desired, converted to a pharmaceutically acceptable salt.

B. Compounds of Formula I Wherein B is $NH_2$.

Compound of Formula I wherein B is $NH_2$ are preferably prepared by converting the compound of Formula B to the corresponding phthalimide compound of Formula C, and then hydrolyzing the phthalimide group, as shown in the following reaction scheme:

Reaction Scheme IV

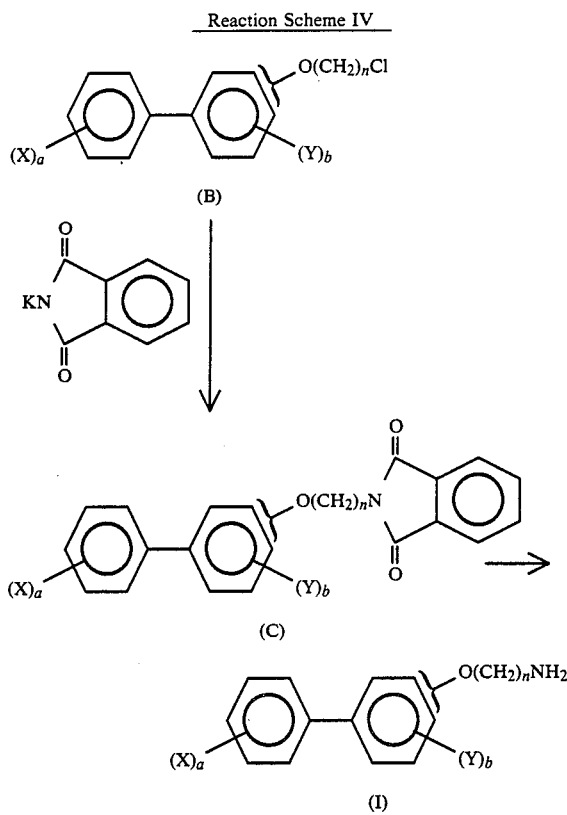

In carrying out this conversion, the compound of Formula B is dissolved in an inert aprotic organic solvent such as tetrahydrofuran, N-methylpyrrolidinone, or preferably, N,N-dimethylformamide. To this solution is added about 1.0-1.5, preferably about 1.05, molar equivalents of a metal salt of phthalimide, preferably potassium phthalimide. The reaction mixture is heated to about 60°-135° C., preferably about 130° C., for 1-24 hours, preferably about 8 hours.

The product of Formula C., an N-(3- or 4-biphenyloxyalkyl)phthalimide, may be isolated by conventional means. It is then hydrolyzed by reacting with an aqueous solution of a strong base, or preferably, by reaction with from about 1 to about 5, preferably about 1.5, molar equivalents of hydrazine in a polar organic or aqueous-organic solvent such as methanol or, preferably, aqueous ethanol. The reaction is maintained at from about 25° C. to reflux temperature, preferably at reflux temperature, for about 1-12, preferably about 3, hours. The resulting optionally substituted 3- or 4-biphenyloxyalkylamine compound of Formula I is then isolated by conventional means and, if desired, may be converted to a corresponding pharmaceutically acceptable salt.

C. Salts of Compounds of Formula I

All of the compounds of Formula I may be converted to their acid addition salts, by virtue of the presence of the amine terminating the alkyl side chain.

The compounds of Formula I in free base form may be converted to the acid addition salts by treating with a stoichiometric excess of the appropriate organic or inorganic acid, such as, for example, phosphoric, citric, pyruvic, hydrochloric or sulfuric acid and the like. Typically, the free base is dissolved in a polar organic solvent such as ethanol or methanol, and the acid added thereto. The temperature is maintained at between about 0° C. and 50° C. The resulting acid addition salt precipitates spontaneously or may be brought out of solution with a less polar solvent.

The acid addition salts of the compounds of Formula I may be decomposed to the corresponding free bases by treating with a stoichiometric excess of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of a compound of Formula I with a slight stoichiometric excess of an acid of a lower pKa than the acid component of the starting salt. This conversion is carried out at a temperature between about 0° C. and the boiling point of the solvent being used as the medium for the procedure.

In summary the compounds of the present invention are made by the procedures (i) and (ii) outlined below.

(i) The process for preparing compounds of the formula

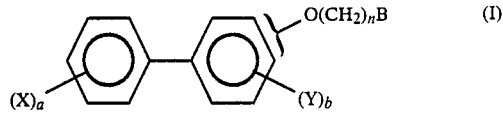

and the pharmaceutically acceptable acid addition salts thereof, wherein:
  a is an integer of 0-3;
  b is an integer of 0-2;
  n is an integer of 3-12;
  each X and each Y are independently halo, —$R^1$, —alkoxy, or —phenyl; and
  B is selected from the group consisting of:
  —$NR^1R^2$, —$NR^1(CH_2CH_2OH)$,

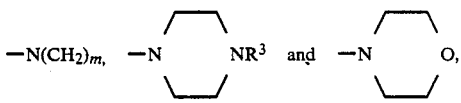

in which
  $R^1$ and $R^2$ are independently H, alkyl or cycloalkyl;
  $R^3$ is H, alkyl or $CH_2CH_2OH$; and
  m is an integer of 3-8,
comprises:
  (a) reacting a compound of the formula:

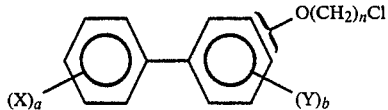

wherein X, Y, a, b and n are as defined above, with an appropriate amine of the formula HB, wherein B is as defined above; or
  (b) converting the free base of the compound of Formula I with an acid to a pharmaceutically acceptable acid addition salt; or (c) converting an acid addition salt of the compound of Formula I with a base to the corresponding free base; or (d) converting an acid addition salt of the compound of Formula I to another pharmaceutically acceptable acid addition salt.

(ii) Alternatively, a process for preparing a compound of Formula I, above, wherein B is NH₂, comprises hydrolyzing a compound of the formula

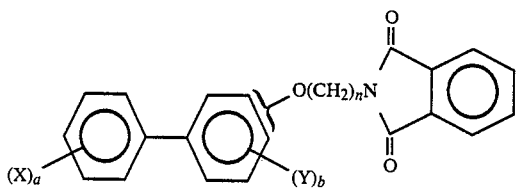

wherein X, Y, a, b, and n are as defined herein.

Utility and Administration

The compounds of Formula I have been shown in standard laboratory tests to inhibit inflammation in mammals. Accordingly, the compounds of Formula I, their salts, and pharmaceutical compositions containing them, may be used in inhibiting, preventing, or controlling inflammation in mammals. Anti-inflammatory activity can be determined by the method described by C. M. Pearson in *Proc.Soc.Exp.Biol.Med.*, 91:95–101, (1956) utilizing adjuvant-induced arthritis in rats. This method is described in detail in Example 12 hereinbelow. In addition, acute inflammatory activity can be determined by inhibition of carrageenan-induced pleural inflammation in rats (as described in the Proceedings of the Society for Experimental Biology and Medicine, 1968, Vol. 127, p. 597 and the Journal of Pharmacology and Experimental Therapeutics, 1969, Vol 168, p. 199.) or by inhibition of topical inflammation caused by croton oil, arachidonic acid or oxazolone. Anti-inflammatory activity can also be determined by in vitro biological assays in which the ability of the compounds to inhibit chemotaxis, as described in the Journal of Experimental Medicine, 1962, Vol 115, p. 453, or to inhibit the enzyme phospholipase $A_2$, or to inhibit the generation of superoxide from polymorphonuclear leucocytes are tested.

The compounds of Formula I may also be useful in preventing, relieving or controlling the associated pain of various inflammatory conditions.

Administration of the active compounds and salts described herein can be effected via any medically acceptable mode of administration for agents which control inflammation and associated pain. These methods include but are not limited to oral, parenteral and otherwise systemic, or topical routes of administration. Oral or topical administration is preferred, depending of course, on the disorder being treated. The compounds are administered in a therapeutically effective amount either alone or in combination with a suitable pharmaceutically acceptable excipient.

Depending on the intended mode of administration, the compounds of this invention may be incorporated in any pharmaceutically acceptable dosage form, such as, for example, tablets, suppositories, pills, capsules, powders, liquids, suspensions, emulsions, aerosols, or the like. Preferable means of administration are unit dosage forms suitable for single administration of precise dosages, or sustained release dosage forms for continuous administration. Preferably the dosage form will include a pharmaceutically acceptable excipient and an active compound of Formula I or a pharmaceutically acceptable salt thereof, and, in addition, may include other medicinal agents, pharmaceutical agents, carriers, excipients, adjuvants, stabilizers, etc. Depending on parameters such as mode of administration, type of composition, and activity of the compound, the pharmaceutical composition may contain 1–99 percent by weight active ingredient with the remainder being excipient.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose, and magnesium carbonate. An example of a solid dosage form of the compounds of this invention is a suppository containing propylene glycol as the carrier. Liquid pharmaceutically administerable dosage forms can, for example, comprise a solution or suspension of an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Penna., 16th Edition, 1980. The composition or formulation to be administered will, in any event, contain a quantity of the active compound(s) in an amount effective to alleviate the symptoms of the subject being treated.

For oral administration, a pharmaceutically acceptable non-toxic dosage form may contain any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such dosage forms may contain 1%–99% active ingredient, preferably 25–70%.

For topical administration, an appropriate dosage form will comprise an effective amount of a compound of Formula I in admixture with a pharmaceutically acceptable non-toxic carrier. A suitable range of composition would be 0.1%–10%, preferably 1–2%, active ingredient, and the balance carrier. The concentration of active ingredient in pharmaceutical compositions suitable for topical application will vary depending upon the therapeutic activity of the particular active ingredient and the medical condition to be treated. Suitable dosage forms for topical application of the compounds of this invention include but are not limited to creams, ointments, lotions, emulsions and solutions.

For example, a suitable ointment for topical application of compounds of the instant invention may contain 15–45% by weight of a saturated fatty alcohol having 16 to 24 carbon atoms, such as cetyl alcohol, stearyl alcohol, behenyl alcohol, and the like, and 45–85% of a glycol solvent such as propylene glycol, polyethylene glycol, dipropylene glycol, and mixtures thereof. In addition, the ointment may contain 0–15% by weight of a plasticizer (e.g., polyethylene glycol, 1,2,6-hexanetriol, sorbitol, glycerol, and the like), 0–15% by weight of a coupling agent such as a saturated fatty acid having from 16 to 24 carbon atoms, (e.g., stearic acid, palmitic acid or behenic acid) a fatty acid amide (e.g., oleamide, palmitamide, stearamide or behenamide) or an ester of a fatty acid having from 16 to 24 carbon atoms, (e.g., sorbitol monostearate, polyethylene glycol monostearate, polypropylene glycol or the corresponding monoester of other fatty acids such as oleic acid and palmitic acid), and 0–20% by weight of a penetrant such as dimethyl sulfoxide or dimethylacetamide.

The amount of active compound administered will, of course, depend on the subject being treated, the severity of the affliction, the manner of administration and the judgment of the prescribing physician. However, a therapeutically effective dosage of compounds of the instant invention is in the range of 1–100 mg/kg/day, preferably about 10–30 mg/kg/day, and most preferably about 25 mg/kg/day. For an average 70 kg human, this would amount to 70 mg –7 g per day, or preferably amount 1.5 g/day.

Preferred Embodiments

A preferred group of the family of compounds of this invention are those compounds of Formula I wherein B is —NR$^1$R$^2$ where R$^1$ and R$^2$ are each independently hydrogen, methyl or ethyl.

Another preferred group are those compounds of Formula I wherein n is at least 6, preferably 6–10. Among these, a preferred subgroup includes those compounds of Formula I wherein a and b are 0, B is —NR$^1$R$^2$ where R$^1$ and R$^2$ are each independently hydrogen, methyl or ethyl, and the alkoxyamino side chain is in the 4- position.

Yet another preferred subgroup of the family of compounds of the present invention are those compounds of Formula I wherein a and b are each independently 0, 1 or 2, and either a or b is at least 1. More preferred embodiments of this subgroup are compounds of Formula I wherein X and/or Y, if present, are attached at the 2-, 6-, 2'- and/or 6'- positions of the biphenyl nucleus, and n is an integer of at least 4. Especially preferred among these are compounds wherein n is an integer of 6 to 8, the alkoxyamino side chain is attached at the 4position and B is —NR$^1$R$^2$ where R$^1$ and R$^2$ are each independently hydrogen, methyl or ethyl.

Particularly preferred are those compounds, and their pharmaceutically acceptable salts, selected from the group consisting of:
7-(4-biphenyloxy)-1-dimethylaminoheptane; and
6-(2-,6-dimethyl-4-biphenyloxy)-1-dimethylaminohexane.

Of course all of the preferred compounds include in their definitions their pharmaceutically acceptable salts.

The following preparations and examples serve to illustrate the invention; they should not be construed as in any way narrowing or limiting the scope of the invention as claimed.

PREPARATION 1

(a) Synthesis of 2,6-Dimethyl-4-methoxybiphenyl

To a mixture of 2,6-dimethyl-4-bromoanisole (4.14 g) and tetrakis (triphenylphosphine) palladium (0.69 g) in toluene (40 ml) and 2.0 molar aqueous sodium carbonate (20 ml) was added phenylboric acid (2. 7 g) in ethanol (10 ml). The reaction was heated at reflux for 16 hours, at which time a solution of phenylboric acid (1.0 g) in ethanol (3 ml) was added. The reaction was heated at reflux for a further 6 hours and then cooled to 25° C., and 30% hydrogen peroxide (1.0 ml) was added. The mixture was stirred for one hour, then poured into water and extracted with ether. The organic phase was dried and evaporated and the residue was chromatographed on silica gel, eluting with 9:1 hexane either, so as to afford 2,6-dimethyl-4-methoxybiphenyl.

PREPARATION 2

(a) Synthesis of 2,6-Dimethyl-4-hydroxybiphenyl 2,6-dimethyl-4-methoxybiphenyl (3.0 g), acetic acid (30 ml) and 48% aqueous hydrobromic acid (30 ml) were heated at reflux temperature for 4 hours. The mixture was then cooled, poured into water and extracted with ether. After extracting the organic solution with aqueous sodium hydroxide, the aqueous extract was acidified with aqueous hydrochloric acid and further extracted with ether. The resulting extract was dried and evaporated and the residue was recrystallized from acetone/hexane to afford 2,6-dimethyl-4-hydroxybiphenyl, mp 128°–130° C.

(b) In a similar manner, but substituting other appropriately substituted 3- and 4- methoxybiphenyls, prepared by the method described in Preparation 1, above, the following compounds are prepared:
2-methyl-3-hydroxybiphenyl;
2-methyl-4-hydroxybiphenyl;
2-methoxy-3-hydroxybiphenyl;
2-methoxy-4-hydroxybiphenyl;
2'-methyl-3-hydroxybiphenyl;
2'-methyl-4-hydroxybiphenyl;
2',6'-dimethyl-3-hydroxybiphenyl;
2',6'-dimethyl-4-hydroxybiphenyl;
2,6-dimethoxy-3-hydroxybiphenyl;
2,6-dimethoxy-4-hydroxybiphenyl;
2',6'-diethyl-3-hydroxybiphenyl;
2',6'-diethyl-4-hydroxybiphenyl;
2,2'-dimethyl-3-hydroxybiphenyl;
2,2'-dimethyl-4-hydroxybiphenyl;
2,2'-diethyl-3-hydroxybiphenyl;
2,2'-diethyl-4-hydroxybiphenyl;
2,2'-dimethoxy-3-hydroxybiphenyl;
2,2'-dimethoxy-4-hdroxybiphenyl;
2,2',6-trimethyl-3-hydroxybiphenyl;
2,2',6-trimethyl-4-hydroxybiphenyl;
2,2',6,6'-tetramethyl-3-hydroxybiphenyl, and
2,2',6,6'-tetramethyl-4-hydroxybiphenyl.

PREPARATION 3

Synthesis of
1-(p-toluenesulphonyloxy)-ω-chloroalkanes (a)
1-(p-toluenesulfonyloxy)-6-chlorohexane.

Paratoluenesulfonyl chloride (48 g) was added to a mixture of 6-chlorohexanol (32.6 g) and pyridine (120 ml). After stirring for two hours at 0° C., the mixture was added to ice and the organic phase extracted with ethyl acetate. The extract was washed with cold dilute hydrochloric acid, water and cold dilute sodium bicarbonate, dried with magnesium sulfate, and evaporated, to yield 1-(p-toluenefonyloxy)-6-chlorohexane as an oil.
(b) In a similar manner, using the appropriate corresponding ω-chloroalkanols, the following compounds were prepared:

1-(p-toluenesulfonyloxy)-4-chlorobutane;
1-(p-toluenesulfonyloxy)-5-chloropentane;
1-(p-toluenesulfonyloxy)-7-chloroheptane;
1-(p-toluenesulfonyloxy)-8-chlorooctane;
1-(p-toluenesulfonyloxy)-9-chlorononane.

(c) The following compounds are similarly prepared:
1-(p-toluenesulfonyloxy)-3-chloropropane;
1-(p-toluenesulfonyloxy)-10-chlorodecane;
1-(p-toluenesulfonyloxy)-11-chloroundecane;
1-(p-toluenesulfonyloxy)-12-chlorododecane.

PREPARATION 4

Preparation of the Biphenyloxy chloroalkanes of Formula B (a) Synthesis of 1-(4-biphenyloxy)-6-chlorohexane.

A mixture of 4-hydroxybiphenyl (34 g), 1-(p-toluenesulfonyloxy)-6-chlorohexane (60 g), anhydrous potassium carbonate (60 g) and dimethylformamide (400 ml) was stirred at 60° C. for 6 hours. Excess potassium carbonate was removed by filtration. Water and ethyl acetate were then added and the resultant solution washed with water, dried with magnesium sulfate and evaporated. The resulting crude residue was then dissolved in ethyl acetate/hexane and recrystallized to yield 1-(4-biphenyloxy)-6-chlorohexane.

(b) In a similar manner, but using the appropriate corresponding 1-(p-toluenesulfonyloxy)-ω-chloroalkane, the synthesis of which is described in Preparation 3, and an appropriately substituted 3- or 4-hydroxybiphenyl, the following compounds were prepared:
1-(4-biphenyloxy)-4-chlorobutane;
1-(4-biphenyloxy)-5-chloropentane;
1-(4-biphenyloxy)-7-chloroheptane;
1-(4-biphenyloxy)-8-chlorooctane;
1-(4-biphenyloxy)-9-chlorononane;
1-(3-biphenyloxy)-6-chlorohexane;
1-(3-biphenyloxy)-8-chlorooctane;
1-(2,6-dimethyl-4-biphenyloxy)-4-chlorobutane;
1-(2,6-dimethyl-4-biphenyloxy)-6-chlorohexane;
1-(2,6-dimethyl-4-biphenyloxy)-8-chlorooctane.

(c) The following compounds of Formula B are similarly prepared;
1-(3-biphenyloxy)-3-chloropropane;
1-(4-biphenyloxy)-3-chloropropane;
1-(3-biphenyloxy)-4-chlorobutane;
1-(3-biphenyloxy)-5-chloropentane;
1-(3-biphenyloxy)-9-chlorononane;
1-(3-biphenyloxy)-10-chlorodecane;
1-(4-biphenyloxy)-10-chlorodecane;
1-(3-biphenyloxy)-11-chloroundecane;
1-(4-biphenyloxy)-11-chloroundecane;
1-(3-biphenyloxy)-12-chlorododecane;
1-(4-biphenyloxy)-12-chlorododecane;
1-(2-methyl-4-biphenyloxy)-6-chlorohexane;
1-(2-methyl-4-biphenyloxy)-8-chlorooctane;
1-(2-chloro-3-biphenyloxy)-3-chloropropane;
1-(2-chloro-4-biphenyloxy)-3-chloropropane;
1-(6-methoxy-3-biphenyloxy)-5-chloropentane;
1-(2-methoxy-4-biphenyloxy)-5-chloropentane;
1-(2'-methyl-3-biphenyloxy)-4-chlorobutane;
1-(2'-methyl-4-biphenyloxy)-4-chlorobutane;
1-(2'-bromo-3-biphenyloxy)-6-chlorohexane;
1-(2'-bromo-4-biphenyloxy)-6-chlorohexane;
1-(2,6-difluoro-3-biphenyloxy)-8-chlorooctane;
1-(2,6-difluoro-4-biphenyloxy)-8-chlorooctane;
1-(2,6-dimethoxy-3-biphenyloxy)-9-chlorononane;
1-(2,6-dimethoxy-4-biphenyloxy)-9-chlorononane;
1-(2',6'-dimethyl-3-biphenyloxy)-4-chlorobutane;
1-(2',6'-dimethyl-4-biphenyloxy)-4-chlorobutane;
1-(2',6'-diethyl-3-biphenyloxy)-5-chloropentane;
1-(2',6'-diethyl-4-biphenyloxy)-5-chloropentane:
1-(2',6'-dichloro-3-biphenyloxy)-6-chlorohexane;
1-(2',6'-dichloro-4-biphenyloxy)-6-chlorohexane;
1-(6'-chloro-2'-ethyl-3-biphenyloxy)-7-chloroheptane;
1-(6'-chloro-2'-ethyl-4-biphenyloxy)-7-chloroheptane;
1-(6-methyl-2-chloro-3-biphenyloxy)-8-chlorooctane;
1-(6-methyl-2-chloro-4-biphenyloxy)-8-chlorooctane;
1-(2,2'-dimethyl-3-biphenyloxy)-4-chlorobutane;
1-(2,2'-dimethyl-4-biphenyloxy)-4-chlorobutane;
1-(2,2'-diethyl-3-biphenyloxy)-5-chloropentane;
1-(2,2'-diethyl-4-biphenyloxy)-5-chloropentane;
1-(2,2',6,6'-tetramethyl-3-biphenyloxy)-4-chlorobutane
1-(2,2',6,6'-tetramethyl-4-biphenyloxy)-4-chlorobutane;
1-(2,2',6,6'-tetrafluoro-3-biphenyloxy)-5-chloropentane;
1-(2,2',6,6'-tetrafluoro-4-biphenyloxy)-5-chloropentane;
1-(2,2',6,6'-tetramethyl-3-biphenyloxy)-6-chlorohexane;
1-(2,2',6,6'-tetramethyl-4-biphenyloxy)-6-chlorohexane;
1-(2,2',6-trimethyl-3-biphenyloxy)-7-chloroheptane;
1-(2,2',6-trimethyl-4-biphenyloxy)-7-chloroheptane;
1-(2,2',6'-trimethyl-3-biphenyloxy)-8-chlorooctane;
1-(2,2',6'-trimethyl-4-biphenyloxy)-8-chlorooctane;
1-(2',6,6'-trifluoro-3-biphenyloxy)-9-chlorononane;
1-(2', 6,6'-trifluoro-4-biphenyloxy)-9-chlorononane;
1-(5-methyl-3-biphenyloxy)-3-chloropropane;
1-(3-methyl-4-biphenyloxy)-3-chloropropane;
1-(3'-ethoxy-3-biphenyloxy)-7-chloroheptane;
1-(3'-ethoxy-4-biphenyloxy)-7-chloroheptane;
1-(3',5'-difluoro-3-biphenyloxy)-10-chlorodecane;
1-(3',5'-difluoro-4-biphenyloxy)-10-chlorodecane;
1-(4'-phenyl-3-biphenyloxy)-6-chlorohexane;
1-(4'-phenyl-4-biphenyloxy)-6-chlorohexane;
1-(6-phenyl-3-biphenyloxy)-8-chlorooctane;
1-(2-phenyl-4-biphenyloxy)-8-chlorooctane;
1-(3-methyl-4-biphenyloxy)-7-chloroheptane;
1-(4-methyl-3-biphenyloxy)-7-chloroheptane;
1-(3',4',5'-triethyl-3-biphenyloxy)-5-chloropentane; and
1-(3',4',5'-triethyl-4-biphenyloxy)-5-chloropentane.

PREPARATION 5

Synthesis of N-[(3- or 4-biphenyloxy)alkyl]phthalimides of Formula C.

(a) N-[6-(4-biphenyloxy)hexyl]phthalimide.

A solution of 1-(4-biphenyloxy)-6-chlorohexane (10.0 g) and potassium phthalimide (9.0 g) in dimethylformamide (100 ml) was heated at 140° C. for 4 hours. The cooled solution was poured into water (900 ml) and filtered to yield N-[6-(4-biphenyloxy) hexyl]phthalimide. (b) In a similar manner, but using the appropriate corresponding optionally substituted 1-(3- or 4-biphenyloxy)-ω-chloroalkane, obtained as described in Preparation 4, the following compounds of Formula C were prepared:
N-[4-(4-biphenyloxy)butyl]phthalimide;
N-[5-(4-biphenyloxy)pentyl]phthalimide;
N-[7-(4-biphenyloxy)heptyl]phthalimide;
N-[8-(4-biphenyloxy)octyl]phthalimide;
N-[9-(4-biphenyloxy)nonyl]phthalimide;
N-[6-(3-biphenyloxy)hexyl]phthalimide;
N-[8-(3-biphenyloxy)octyl]phthalimide;
N-[4-(2,6-dimethyl-4-biphenyloxy)butyl]phthalimide;
N-[6-(2,6-dimethyl-4-biphenyloxy)hexyl]phthalimide;
N-[8-(2,6-dimethyl-4-biphenyloxy)octyl]phthalimide;

(c) Following the procedures set forth in Paragraphs (a) and (b) of this Preparation, but using instead other appropriate optionally substituted 1-(3- or 4-biphenyloxy)-ω-chloroalkanes, obtained as described in Preparation 4, the following representative compounds of Formula C are prepared:

N-[3-(3-biphenyloxy)propyl]phthalimide;
N-[3-(4-biphenyloxy)propyl]phthalimide;
N-[4-(3-biphenyloxy)butyl]phthalimide;
N-[5-(3-biphenyloxy)pentyl]phthalimide;
N-[7-(3-biphenyloxy)heptyl]phthalimide;
N-[9-(3-biphenyloxy)nonyl]phthalimide;
N-(10-(4-biphenyloxy)decyl]phthalimide;
N-[11-(3-biphenyloxy)undecyl]phthalimide;
N-[11-(4-biphenyloxy)undecyl]phthalimide;
N-[12-(3-biphenyloxy)dodecyl]phthalimide;
N-[12-(4-biphenyloxy)dodecyl]phthalimide;
N-[3-(2-chloro-3-biphenyloxy)propyl]phthalimide;
N-[3-(2-chloro-4-biphenyloxy)propyl]phthalimide;
N-[5-(6-methoxy-3-biphenyloxy)pentyl]phthalimide;
N-[5-(6-methoxy-4-biphenyloxy)pentyl]phthalimide;
N-[4-(2'-methyl-3-biphenyloxy)butyl]phthalimide;
N-[4-(2'-methyl-4-biphenyloxy)butyl]phthalimide;
N-[6-(2'-bromo-3-biphenyloxy)hexyl]phthalimide;
N-[6-(2'-bromo-4-biphenyloxy)hexyl]phthalimide;
N-[8-(2,6-dibromo-3-biphenyloxy)octyl]phthalimide;
N-[8-(2,6-dibromo-4-biphenyloxy)octyl]phthalimide;
N-[9-(2,6-dimethoxy-3-biphenyloxy)nonyl]phthalimide;
N-[9-(2,6-dimethoxy-4-biphenyloxy)nonyl]phthalimide;
N-[4-(2',6'-dimethyl-3-biphenyloxy)buty]phtha-limide;
N-[4-(2',6'-dimethyl-4-biphenyloxy)butyl]phthalimide;
N-[5-(2',6'-diethyl-3-biphenyloxy)pentyl]phthalimide;
N-[5-(2',6'-diethyl-4-biphenyloxy)pentyl]phthalimide;
N-[6-(2',6'-dichloro-3-biphenyloxy)hexyl]phthalimide;
N-[6-(2',6'-dichloro-4-biphenyloxy)hexyl]phthalimide;
N-[7-(6'-chloro-2'-ethyl-3-biphenyloxy)heptyl]phthalimide;
N-[7-(6'-chloro-2'-ethyl-4-biphenyloxy)heptyl]phthalimide;
N-[8-(2-chloro-6-methyl-3-biphenyloxy)octyl]phthalimide;
N-[8-(2-chloro-6-methyl-4-biphenyloxy)octyl]phthalimide;
N-[4-(2,2'-dimethyl-3-biphenyloxy)butyl]phthalimide;
N-[4-(2,2'-dimethyl-4-biphenyloxy)butyl]phthalimide;
N-[5-(2,2'-diethyl-3-biphenyloxy)pentyl]phthalimde;
N-[5-(2,2'-diethyl-4-biphenyloxy)pentyl]phthalimide;
N-[4-(2,2',6,6'-tetramethyl-3-biphenyloxy)butyl]phthalimide
N-[4-(2,2',6,6'-tetramethyl-4-biphenyloxy)butyl]phthalimide;
N-[5-(2,2',6,6'-tetrachloro-3-biphenyloxy)pentyl]phthalimide;
N-[5-(2,2-,6'6'-tetrachloro-4-biphenyloxy)pentyl]phthalimide;
N-[6-(2,2',6,6'-tetramethyl-3-biphenyloxy)hexyl]phthalimide;
N-[6-(2,2',6,6'-tetramethyl-4-biphenyloxy)hexyl]phthalimide;
N-[7-(2,2',6trimethyl-3-biphenyloxy)heptyl]phthalimide;
N-[7-(2,2',6-trimethyl-4-biphenyloxy)heptyl]phthalimide;
N-[8-(2,2',6'-trimethyl-3-biphenyloxy)octyl]phthalimide;
N-[8-(2,2',6'-trimethyl-4-biphenyloxy)octyl]phthalimide;
N-[9-(2',6,6'-trifluoro-3-biphenyloxy)nonyl]phthalimide;
N-[9-(2',6,6'-trifluoro-4-biphenyloxy)nonyl]]phthalimide;
N-[3-(5-methyl-3-biphenyloxy)propyl]phthalimide;
N-[4-(5-methyl-4-biphenyloxy)butyl]phthalimide;
N-[7-(3'-ethoxy-3-biphenyloxy)heptyl]phthalimide;
N-[7-(3'-ethoxy-4-biphenyloxy)heptyl]phthalimide;
N-[10-(3',5'-dibromo-3-biphenyloxy)decyl]phthalimide;
N-[10-(3',5'-dibromo-4-biphenyloxy)decyl]phthalimide;
N-[6-(4'-phenyl-3-biphenyloxy)hexyl]phthalimide;
N-[6-(4'-phenyl-4-biphenyloxy)hexyl]phthalimide;
N-[8-(6-phenyl-3-biphenyloxy)octyl]phthalimide;
N-[8-(2-phenyl-4-biphenyloxy)octyl]phthalimide;
N-[7-(3-methyl-4-biphenyloxy)heptyl]phthalimide;
N-[7-(4-methyl-3-biphenyloxy)heptyl]phthalimide;
N-[5-(3',4',5'-triethyl-3-biphenyloxy)pentyl]phthalimide;
N-[5-(3',4',5'-triethyl-4-biphenyloxy)pentyl]phthalimide;
N-[6-(3,5-diethyl-4-biphenyloxy)hexyl]phthalimide;
N-[4-(6'-methyl-3-biphenyloxy)butyl]phthalimide; and
N-[4-(6'-methyl-4-biphenyloxy)butyl]phthalimide.

EXAMPLE I

Preparation of 6-(4-Biphenyloxy)-1-aminohexane and Related Compounds of Formula I (a) A mixture of N-[6-(4-biphenyloxy)hexyl]phthalimide (17 g), ethanol (500 ml) and hydrazine hydrate (10 ml) was heated at reflux for 16 hours, cooled to room temperature, filtered, and evaporated to dryness. The remaining material was stirred with dichloromethane (500 ml), filtered and evaporated to dryness. The crude product was chromatographed on silica gel, eluting with 95:5 dichloromethane:methanolic ammonia, yielding 6-(4-biphenyloxy)-1-aminohexane as an oil, which was converted to the hydrochloride salt, (m.p. 201°-202° C.), according to the method of Example 3.

(b) Following the procedure described above in paragraph (a) of this Example, but substituting the appropriate optionally substituted N-(3- or 4-biphenyloxy)alkyl]phthalimide, prepared according to the method of Preparation 5, the following compounds of Formula I were prepared and converted to pharmaceutically acceptable salts:

4-(4-biphenyloxy)-1-aminobutane, as the hydrochloride, m.p. 202°-205° C.;
4-(2,6-dimethyl-4-biphenyloxy)-1-aminobutane, as the p-toluenesulphonate, m.p. 115°-120° C.;
5-(4-biphenyloxy)-1-aminopentane, as the hydrochloride, m.p. 244°-246°° C.;
6-(3-biphenyloxy)-1-aminohexane, as the hydrochloride, m.p. 120°-122° C.;
6-(2,6-dimethyl-4-biphenyloxy)-1-aminohexane, as the p-toluenesulphonate, m.p. 147°-148° C.;
6-(4'-methoxy-4-biphenyloxy)-1-aminohexane as the hydrochloride, m.p. 265°-273° C.;
7-(4-biphenyloxy)-1-aminoheptane, as the hydrochloride monohydrate, m.p. 228°-230° C.; and
8-(4-biphenyloxy)-1-aminooctane, as the hydrochloride, m.p. 179°-182° C.

(c) In a similar manner, the following compounds of Formula I are prepared:
3-(3-biphenyloxy)-1-aminopropane;
3-(4-biphenyloxy)-1-aminopropane;
4-(3-biphenyloxy)-1-aminobutane;
5-(3-biphenyloxy)-1-aminopentane;
7-(3-biphenyloxy)-1-aminoheptane;
10-(3-biphenyloxy)-1-aminodecane;

10-(4-biphenyloxy)-1-aminodecane;
11-(3-biphenyloxy)-1-aminoundecane;
11-(4-biphenyloxy)-1-aminoundecane;
12-(3-biphenyloxy)-1-aminododecane;
12-(4-biphenyloxy)-1-aminododecane;
3-(2-chloro-3-biphenyloxy)-1-aminopropane;
3-(2-chloro-4-biphenyloxy)-1-aminopropane;
5-(6-methoxy-3-biphenyloxy)-1-aminopentane;
5-(2-methoxy-4-biphenyloxy)-1-aminopentane;
4-(2'-methyl-3-biphenyloxy)-1-aminobutane;
4-(2'-methyl-4-biphenyloxy)-1-aminobutane;
6-(2'-bromo-3-biphenyloxy)-1-aminohexane;
6-(2'-bromo-4-biphenyloxy)-1-aminohexane;
8-(2,6-dibromo-3-biphenyloxy)-1-aminooctane;
8-(2,6-dibromo-4-biphenyloxy)-1-aminooctane;
9-(2,6-dimethoxy-3-biphenyloxy)-1-aminononane;
9-(2,6-dimethoxy-4-biphenyloxy)-1-aminononane;
4-(2',6'-dimethyl-3-biphenyloxy)-1-aminobutane;
4-(2',6'-dimethyl-4-biphenyloxy)-1-aminobutane;
5-(2',6'-diethyl-3-biphenyloxy)-1-aminopentane;
5-(2',6'-diethyl-4-biphenyloxy)-1-aminopentane;
6-(2',6'-dichloro-3-biphenyloxy)-1-aminohexane;
6-(2',6'-dichloro-3-biphenyloxy)-1-aminohexane;
7-(2'-ethyl-6'-chloro-3-biphenyloxy)-1-aminoheptane;
7-(2'-ethyl-6'-chloro-4-biphenyloxy)-1-aminoheptane;
8-(2-chloro-6-methyl-3-biphenyloxy)-1-aminooctane;
8-(2-chloro-6-methyl-4-biphenyloxy)-1-aminooctane;
4-(2,2'-dimethyl-3-biphenyloxy)-1-aminobutane;
4-(2,2'-dimethyl-4-biphenyloxy)-1-aminobutane;
5-(2,2'-diethyl-3-biphenyloxy)-1-aminopentane;
5-(2,2'-diethyl-4-biphenyloxy)-1-aminopentane;
4-(2,2',6,6'-tetramethyl-3-biphenyloxy)-1-aminobutane;
4-(2,2',6,6'-tetramethyl-4-biphenyloxy)-1-aminobutane;
5-(2,2',6,6'-tetrachloro-3-biphenyloxy)-1-aminopentane;
5-(2,2',6,6'-tetrachloro-4-biphenyloxy)-1-aminopentane;
6-(2,2',6,6'-tetramethyl-3-biphenyloxy)-1-aminohexane;
6-(2,2',6,6'-tetramethyl-4-biphenyloxy)-1-aminohexane;
7-(2,2',6-trimethyl-3-biphenyloxy)-1-aminoheptane;
7-(2,2',6-trimethyl-4-biphenyloxy)-1-aminoheptane;
8-(2,2',6'-trimethyl-3-biphenyloxy)-1-aminooctane;
8-(2,2',6'-trimethyl-4-biphenyloxy)-1-aminooctane;
9-(2',6,6'-trifluoro-3-biphenyloxy)-1-aminononane;
9-(2',6,6'-trifluoro-4-biphenyloxy)-1-aminononane;
3-(5-methyl-3-biphenyloxy)-1-aminopropane;
4-(3-methyl-4-biphenyloxy)-1-aminobutane;
7-(3'-ethoxy-3-biphenyloxy)-1-aminoheptane;
7-(3'-ethoxy-4-biphenyloxy)-1-aminoheptane;
10-(3',5'-dibromo-3-biphenyloxy)-1-aminodecane;
10-(3',5'-dibromo-4-biphenyloxy)-1-aminodecane;
6-(4'-phenyl-3-biphenyloxy)-1-aminohexane;
6-(4'-phenyl-4-biphenyloxy)-1-aminohexane;
8-(6-phenyl-3-biphenyloxy)-1-aminooctane;
8-(2-phenyl-4-biphenyloxy)-1-aminooctane;
7-(3-methyl-4-biphenyloxy)-1-aminoheptane;
7-(4-methyl-3-biphenyloxy)-1-aminoheptane;
5-(3',4',5'-triethyl-3-biphenyloxy)-1-aminopentane;
5-(3',4',5'-triethyl-4-biphenyloxy)-1-aminopentane;
6-(3,5-diethyl-4-biphenyloxy)-1-aminohexane;
4-(6'-methyl-3-biphenyloxy)-1-aminobutane; and
4-(6'-methyl-4-biphenyloxy)-1-aminobutane.

EXAMPLE 2

Preparation of
6-(4-biphenyloxy)-1-dimethylaminohexane and Related
Compounds of Formula I (a) 1-(4-biphenyloxy)-6-chlorohexane (5.0 g) and ethylene glycol saturated with dimethylamine (60 ml), were heated at reflux for 3 hours using a dry ice condenser. The solution was added to water. The resulting mixture was extracted with ethyl acetate, dried with sodium sulfate and evaporated. The crude product was chromatographed on silica gel, eluting with a solution of dichloromethane:methanolic ammonia (95:5), to yield 6-(4-biphenyloxy)-1-dimethylaminohexane, which was converted to the hydrochloride salt, m.p. 163°-165° C.

(b) Following the procedure described in Paragraph (a) above, but starting with the appropriate 1-(4-biphenyloxy)-1-chloroalkane whose synthesis is described in Preparation 4, above, and an amine of Formula HB in which B has the definition given above in the Summary, the following compounds of Formula I were prepared:

4-(4-biphenyloxy)-1-dimethylaminobutane, as the hydrochloride, m.p. 202°-205° C.;
6-(4-biphenyloxy)-1-dimethylaminohexane, as the hydrochloride, m.p. 163°-165° C.;
6-(4-biphenyloxy)-1-methylaminohexane, as the hydrochloride, m.p. 204°-205° C.;
7-(4-biphenyloxy)-1-dimethylaminoheptane, as the hydrochloride, m.p. 175°-177° C.;
8-(4-biphenyloxy)-1-dimethylaminooctane, as the hydrochloride, m.p. 156°-158° C.; and
9-(4-biphenyloxy)-1-dimethylaminononane, as the hydrochloride, m.p. 167°-168° C.

(c) In a similar manner, the following substitituted compounds of Formula I were prepared from substituted 1-(3- or 4-biphenyloxy)-1-chloroalkanes synthesized according to the method described in Preparation 4(b), above:

6-(2,6-dimethyl-4-biphenyloxy)-1-dimethylaminohexane as the paratoluenesulphonate, m.p. 118°-120° C.;
8-(2,6-dimethyl-4-biphenyloxy)-1-dimethylaminooctane as the paratoluenesulphonate, m.p. 89°-93° C.; and
6-(4'-methoxy-4-biphenyloxy)-1-dimethylaminohexane, as the hydrochloride, m.p. 192°-194° C.

(d) In like manner, the following compounds of Formula I are prepared:

3-(3-biphenyloxy)-1-dimethylaminopropane;
3-(4-biphenyloxy)-1-dimethylaminopropane;
4-(3-biphenyloxy)-1-dimethylaminobutane;
5-(3-biphenyloxy)-1-dimethylaminopentane;
7-(3-biphenyloxy)-1-dimethylaminoheptane;
10-(3-biphenyloxy)-1-dimethylaminodecane;
10-(4-biphenyloxy)-1-dimethylaminodecane;
11-(3-biphenyloxy)-1-dimethylaminoundecane;
11-(4-biphenyloxy)-1-dimethylaminoundecane;
12-(3-biphenyloxy)-1-dimethylaminododecane;
12-(4-biphenyloxyoxy)-1-dimethylaminododecane;
3-(2-chloro-3-biphenyloxy)-1-dimethylaminopropane;
3-(2-chloro-4-biphenyloxy)-1-dimethylaminopropane;
5-(6-methoxy-3-biphenyloxy)-1-dimethylaminopentane;
5-(2-methoxy-4-biphenyloxy)-1-dimethylaminopentane.

(e) Similarly, but substituting other appropriate cyclic or acylic amines for the dimethylamine, the following representative compounds of Formula I are prepared:

4-(3-biphenyloxy)-1-(2-hydroxyethylamino)butane;
4-(4-biphenyloxy)-1-pyrrolidinobutane;
5-(3-biphenyloxy)-1-(N-methyl-N-ethylamino)pentane;
6-(4-biphenyloxy)-1-(4-ethylpiperazino)hexane;
8-(4-biphenyloxy)-1-diisopropylaminooctane;
3-(2-chloro-3-biphenyloxy)-1-piperidinopropane;
3-(2-chloro-4-biphenyloxy)-1-piperidinopropane;

5-(6-methoxy-3-biphenyloxy)-1-(N-methyl-N-n-butylamino)pentane;
5-(2-methoxy-4-biphenyloxy)-1-(N-methyl-N-n-butylamino)pentane;
4-(2'-methyl-3-biphenyloxy)-1-morpholinopropane;
4-(2'-methyl-4-biphenyloxy)-1-morpholinopropane;
6-(2'-bromo-3-biphenyloxy)-1-(4-methylpiperazino)-hexane;
6-(2'-bromo-4-biphenyloxy)-1-(4-methylpiperazino)-hexane;
8-(2,6-dibromo-3-biphenyloxy)-1-ethylaminooctane;
8-(2,6-dibromo-4-biphenyloxy)-1-ethylaminooctane;
9-(2,6-dimethoxy-3-biphenyloxy)-1-azetidinononane;
9-(2,6-dimethoxy-4-biphenyloxy)-1-azetidinononane;
4-(2',6'-dimethyl-3-biphenyloxy)-1(4-(2-hydroxyethyl)-piperazino)butane;
4-(2',6'-dimethyl-4-biphenyloxy)-1(4-(2-hydroxyethyl)-piperazino)butane;
5-(2',6'-diethyl-3-biphenyloxy)-1-ethylaminopentane;
5-(2',6'-diethyl-4-biphenyloxy)-1-ethylaminopentane;
6-(2',6'-dichloro-3-biphenyloxy)-1-(N-methyl-N-ethylamino)hexane;
6-(2',6'-dichloro-4-biphenyloxy)-1-(N-methyl-N-ethylamino)hexane;
7-(2-ethyl-6'chloro-3-biphenyloxy)-1-di-n-propylaminoheptane;
7-(2-ethyl-6'chloro-4-biphenyloxy)-1-di-n-propylaminoheptane;
8-(2-chloro-6-methyl-3-biphenyloxy)-1-pyrrolidinooctane;
8-(2-chloro-6-methyl-4-biphenyloxy)-1-pyrrolidinooctane;
4-(2,2'-dimethyl-3-biphenyloxy)-1-(2-hydroxyethylamino)butane;
4-(2,2'-dimethyl-4-biphenyloxy)-1-(2-hydroxyethylamino)butane;
5-(2,2'-diethyl-3-biphenyloxy)-1-pyrrolidinopentane;
5-(2,2'-diethyl-4-biphenyloxy)-1-pyrrolidinopentane;
4-(2,2',6,6'-tetramethyl-3-biphenyloxy)-1-(4-ethylpiperazino)butane;
4-(2,2',6,6'-tetramethyl-4-biphenyloxy)-1(4-ethylpiperazino)butane;
5-(2,2',6,6'-tetrafluoro-3-biphenyloxy)-1-diethylaminopentane;
5-(2,2',6,6'-tetrafluoro4-biphenyloxy)-1diethylaminopentane;
6-(2,2',6,6'-tetramethyl-3-biphenyloxy)-1-methylaminohexane;
6-(2,2',6,6'-tetramethyl-4-biphenyloxy)-1methylaminohexane;
7-(2,2',6-trimethyl-3-biphenyloxy)-1azetidinoheptane;
7-(2,2',6-trimethyl-4-biphenyloxy)-1azetidinoheptane;
8-(2,2',6'-trimethyl-3-biphenyloxy)-1ethylaminooctane;
8-(2,2',6'-trimethyl-4-biphenyloxy)-1ethylaminooctane;
9-(2',6,6'-trifluoro-3-biphenyloxy)-1piperazinononane;
9-(2',6,6'-trifluoro-4-biphenyloxy)-1piperazinononane;
3-(5-methyl-3-biphenyloxy)-1(2-hydroxyethylamino)propane;
4-(3-methyl-4-biphenyloxy)-1(2-hydroxyethylamino)butane;
7-(3'-ethoxy-3-biphenyloxy)-1-(methyl-n-butylamino)heptane;
7-(3'-ethoxy-4-biphenyloxy)-1-(methyl-n-butylamino)heptane;
10-(3',5'-difluoro-3-biphenyloxy)-1-di-n-propylaminodecane;
10-(3',5'-difluoro-4-biphenyloxy)-1-di-n-propylaminodecane;
6-(4'-phenyl-3-biphenyloxy)-1-(4-methylpiperazinohexane;
6-(4'-phenyl-4-biphenyloxy)-1-pyrrolidinohexane;
8-(6-phenyl-3-biphenyloxy)-1-piperazinooctane;
8-(2-phenyl-4-biphenyloxy)-1-piperazinooctane;
7-(3-methyl-4-biphenyloxy)-1-diethylaminoheptane;
7-(4-methyl-3-biphenyloxy)-1-diethylaminoheptane;
5-(3',4',5'-triethyl-3-biphenyloxy)-1-pyrrolidinopentane;
5-(3',4',5'-triethyl-4-biphenyloxy)-1-pyrrolidinopentane;
4-(6'-methyl-3-biphenyloxy)-1-pyrrolidinobutane; and
4-(6'-methyl-4-biphenyloxy)-1-pyrrolidinobutane.

EXAMPLE 3

Conversion of Free Base to Salt

A twofold stoichiometric excess of 3% hydrochloric acid in methanol is added to a methanolic solution of 1.0 g. of 4-(4-biphenyloxy)-1-aminobutane. Diethyl ether is added until precipitation is complete. The product is filtered, washed with ether, air dried and recrystallized to give 4-(4-biphenyloxy)-1-aminobutane hydrochloride, m.p. 202°–205° C.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 4

Conversion of Salt to Free Base 1.0 g of 4-(4-biphenyloxy)-1-aminobutane hydrochloride suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield 4-(4-biphenyloxy)-1-aminobutane as the free base.

EXAMPLE 5

Direct interchange of acid addition salts 7-(4-biphenyloxy)-1-dimethylaminoheptane acetate (1.0 g) is dissolved in 50 ml water containing a stoichiometric equivalent of sulfuric acid, and the solution evaporated to dryness. The product is suspended in ethanol and filtered, air dried and recrystallized from methanol/acetone to yield 7-(4-biphenyloxy)-1-dimethylaminoheptane bisulfate.

In a similar manner interchanges between other acid addition salts of compounds of Formula I can be made by treating with an appropriate inorganic or organic acid.

EXAMPLES 6-11

In Examples 6 through 11, the active ingredient is 6-(2,6-dimethyl)-4-biphenyloxy)-1-dimethylaminohexane; however other compounds of Formula I and the pharmaceutically acceptable salts thereof may be substituted therein:

EXAMPLE 6

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 7

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 8

| Ingredients | Quantity per tablet, mgs. |
|---|---|
| Active ingredient | 108 |
| lactose | 15 |
| cornstarch | 25 |
| magnesium stearate | 2 |

The above ingredients are mixed and introduced into a hard-shell gelatin capsule.

EXAMPLE 9

| Ingredients | Quantity per tablet, mgs. |
|---|---|
| Active ingredient | 150 |
| lactose | 92 |

The above ingredients are mixed and introduced into a hard-shell gelatin capsule.

EXAMPLE 10

A solution preparation buffered to a pH of 7 is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water | q.s. to 100 ml |

EXAMPLE 11

A topical formulation is prepared as follows.

| The composition contains: | |
|---|---|
| | % wt./wt. |
| Active ingredient | 0.5 |
| Methyl paraben | 0.025 |
| Propyl paraben | 0.015 |
| Sodium lauryl sulfate | 1.0 |
| Propylene glycol | 12.0 |
| Stearyl alcohol | 25.0 |
| White petrolatum | 25.0 |
| Purified water qs. ad. | 100.0 |

The stearyl alcohol and white petrolatum are heated on a steam bath to about 75° C. The other ingredients, previously dissolved in the water and warmed to 75° C., are added with stirring. Stirring is continued until the mixture congeals.

EXAMPLE 12

Determination of Anti-Inflammatory Activity Utilizing Adjuvant-Induced Arthritis In The Rat Protocol:

This procedure is a modification of a system initially described by Pearson, C. M., *Proc.Soc. Exp.Biol.Med.*, 91:95–101 (1956).

Female Simonsen albino rats weighing 160-180 g received 0.1 ml of a suspension in paraffin oil of heat-killed M. butyricum (10 mg/ml) by means of an intradermal injection into the proximal ¼ of the tail on day 0. Beginning on day 1, the test material was administered orally in an aqueous vehicle (0.5 ml/dose) twice each day for 17 days. On day 18 the intensity of the swelling of the four foot pads and tail was determined utilizing a scoring system in which the swelling in the four paws was scored 0–4 for each paw and the tail swelling was scored 0–3, such that the total maximum score was 19. Compounds of the present invention show anti-inflammatory activity when tested by this method.

EXAMPLE 13

Determination Of Anti-Inflammatory Activity Using The Croton Oil-Inflamed Rat Ear Protocol:

A modification of the method of Tonelli et al, *Endocrinology*, 77: 625–634 (1965).

Intact male Simosen albino rats, 21 days old, were anesthetized with ether and the test material was inuncted onto the left ear as follows: 0.05 ml of the vehicle containing the compound in solution was applied to the innter surface of the ear and 0.05 ml of the vehicle was applied to the outer surface. The vehicle consisted of 20% pyridine, 5% distilled water, 74% diethyl ether and 1% croton oil. The rats of the control group received only the vehicle, which served as the inflammatory stimulus. Since the inflammatory agent and test material were given together, the test measures the ability of the test agent to prevent the development of the inflammation, not the ability of the agent to inhibit a pre-induced inflammation. Both ears were removed 6 hr after the agent was applied and a piece of uniform size was punched from each ear with a No. 4 cork bore.

The results are expressed as the difference between the weight of the piece punched from the left (inflamed) ear and that of the right (non-inflamed control) ear.

What is claimed is:

1. A method of preventing, reducing or inhibiting inflammation which method comprises administering to a mammal in need of such treatment a therapeutically effective amount of a compound of the formula:

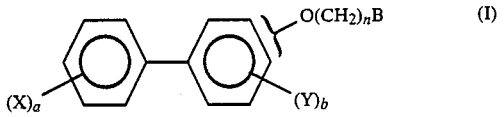

or a pharmaceutically acceptable acid addition salt thereof, wherein:
  a is an integer of 0-3;
  b is an integer of 0-2;
  n is an integer of 3-12; each X and each Y are independently —halo, —R$^1$, —alkoxy, or —phenyl; and
  B is selected from the group consisting of:
  —NR$^1$R$^2$, —NR$^1$(CH$_2$CH$_2$OH),

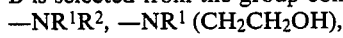
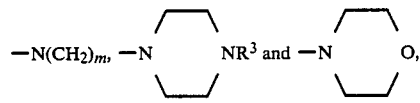

in which
  R$^1$ and R$^2$ are independently H, alkyl or cycloalkyl;
  R$^3$ is H, alkyl or —CH$_2$CH$_2$OH; and
  m is an integer of 3-8.

2. The method of claim 1 in which the compound is 6-(3-biphenyloxy)-1-aminohexane, and the pharmaceutically acceptable acid addition salts thereof.

3. The method of claim 1 in which the compound is 6-(4'-methoxy-4-biphenyloxy)-1-aminohexane, and the pharmaceutically acceptable acid addition salts thereof.

4. The method of claim 21 in which the compound is 6-(4'-methoxy-4-biphenyloxy)-1-dimethylaminohexane, and the pharmaceutically acceptable acid addition salts thereof.

5. The method of claim 1 in which the compound is 5-(4-biphenyloxy)-1-aminopentane, and the pharmaceutically acceptable acid addition salts thereof.

6. The method of claim 1 in which the compound is 6-(4-biphenyloxy)-1-aminohexane, and the pharmaceutically acceptable acid addition salts thereof.

7. The method of claim 1 in which the compound is 7-(4-biphenyloxy)-1-aminoheptane, and the pharmaceutically acceptable acid addition salts thereof.

8. The method of claim 1 in which the compound is 7-(4-biphenyloxy)-1-dimethylaminoheptane, and the pharmaceutically acceptable acid addition salts thereof.

9. The method of claim 1 in which the compound is 8-(4-biphenyloxy)-1-aminooctane, and the pharmaceutically acceptable acid addition salts thereof.

10. The method of claim 1 in which the compound is 8-(4-biphenyloxy)-1-dimethylaminooctane, and the pharmaceutically acceptable acid addition salts thereof.

11. The method of claim 1 in which the compound is 9-(4-biphenyloxy)-1-dimethylaminononane, and the pharmaceutically acceptable acid addition salts thereof.

12. The method of claim 1 in which the compound is 4-(4-biphenyloxy)-1-aminobutane, and the pharmaceutically acceptable acid addition salts thereof.

13. The method of claim 1 in which the compound is 4-(4-biphenyloxy)-1-dimethylaminobutane, and the pharmaceutically acceptable acid addition salts thereof.

14. The method of claim 1 in which the compound is 4-(2,6-dimethyl-4-biphenyloxy)-1-aminobutane, and the pharmaceutically acceptable acid addition salts thereof.

15. The method of claim 1 in which the compound is 6-(2,6-dimethyl-4-biphenyloxy)-1-aminohexane, and the pharmaceutically acceptable acid addition salts thereof.

16. The method of claim 1 in which the compound is 6-(2,6-dimethyl-4-biphenyloxy)-1-dimethylaminohexane, and the pharmaceutically acceptable acid addition salts thereof.

17. The method of claim 1 in which the compound is 8-(2,6-dimethyl-4-biphenyloxy)-1-dimethylaminooctane, and the pharmaceutically acceptable acid addition salts thereof.

18. A method of preventing, reducing or inhibiting localized inflammation and associated pain, which method comprises administering topically to a mammal in need of such treatment a compound of the formula:

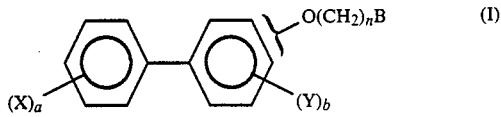

and the pharmaceutically acceptable acid addition salts thereof, wherein:
  a is an integer of 0-3;
  b is an integer of 0-2;
  n is an integer of 3-12;
  each X and each Y are independently —halo, —R$^1$, —alkoxy, or —phenyl; and
  B is selected from the group consisting of:
  —NR$^1$R$^2$, —NR$^1$(CH$_2$CH$_2$OH),

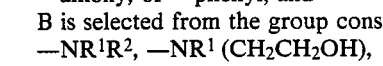
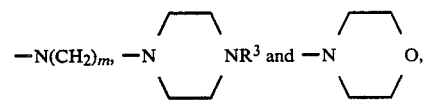

in which
  R$^1$ and R$^2$ are independently H, alkyl or cycloalkyl;
  R$^3$ is H, alkyl or —CH$_2$CH$_2$OH; and
  m is an integer of 3-8.

19. The method of claim 18 in which the compound is 6-(3-biphenyloxy)-1-aminohexane, and the pharmaceutically acceptable acid addition salts thereof.

20. The method of claim 18 in which the compound is 6-(4'-methoxy-4-biphenyloxy)-1-aminohexane, and the pharmaceutically acceptable acid addition salts thereof.

21. The method of claim 18 in which the compound is 6-(4'-methoxy-4-biphenyloxy)-1-dimethyaminohexane, and the pharmaceutically acceptable acid addition salts thereof.

22. The method of claim 18 in which the compound is 5-(4-biphenyloxy)-1-aminopentane, and the pharmaceutically acceptable acid addition salts thereof.

23. The method of claim 18 in which the compound is 6-(4-biphenyloxy)-1-aminohexane, and the pharmaceutically acceptable acid addition salts thereof.

24. The method of claim 18 in which the compound is 7-(4-biphenyloxy)-1-aminoheptane, and the pharmaceutically acceptable acid addition salts thereof.

25. The method of claim 18 in which the compound is 7-(4-biphenyloxy)-1-dimethylaminoheptane, and the pharmaceutically acceptable acid addition salts thereof.

26. The method of claim 18 in which the compound is 8-(4-biphenyloxy)-1-aminooctane, and the pharmaceutically acceptable acid addition salts thereof.

27. The method of claim 18 in which the compound is 8-(4-biphenyloxy)-1-dimethylaminooctane, and the pharmaceutically acceptable acid addition salts thereof.

28. The method of claim 18 in which the compound is 9-(4-biphenyloxy)-1-dimethylaminononane, and the pharmaceutically acceptable acid addition salts thereof.

29. The method of claim 18 in which the compound is 4-(4-biphenyloxy)-1-aminobutane, and the pharmaceutically acceptable acid addition salts thereof.

30. The method of claim 18 in which the compound is 4-(4-biphenyloxy)-1-dimethylaminobutane, and the pharmaceutically acceptable acid addition salts thereof.

31. The method of claim 18 in which the compound is 4-(2,6-dimethyl-4-biphenyloxy)-1-aminobutane, and the pharmaceutically acceptable acid addition salts thereof.

32. The method of claim 18 in which the compound is 6-(2,6-dimethyl-4-biphenyloxy)-1-aminohexane, and the pharmaceutically acceptable acid addition salts thereof.

33. The method of claim 18 in which the compound is 6-(2,6-dimethyl-4-biphenyloxy)-1-dimethylaminohexane, and the pharmaceutically acceptable acid addition salts thereof.

34. The method of claim 18 in which the compound is 8-(2,6-dimethyl-4-biphenyloxy)-1-dimethylaminooctane, and the pharmaceutically acceptable acid addition salts thereof.

* * * * *